United States Patent [19]

Maccecchini

[11] Patent Number: 5,523,323
[45] Date of Patent: Jun. 4, 1996

[54] USE OF PARTIAL AGONISTS OF THE NMDA RECEPTOR TO REDUCE OPIATE INDUCED TOLERANCE AND DEPENDENCE

[76] Inventor: Maria-Luisa Maccecchini, Apt. 2204, 2400 Chestnut St., Philadelphia, Pa. 19103

[21] Appl. No.: 121,100

[22] Filed: Sep. 14, 1993

[51] Int. Cl.$^6$ .............. A61K 31/195; A61K 31/215
[52] U.S. Cl. ............ 514/531; 514/561; 514/567
[58] Field of Search .................. 514/531, 561, 514/567

[56] References Cited

U.S. PATENT DOCUMENTS

| | | | |
|---|---|---|---|
| 4,904,681 | 2/1990 | Cordi et al. | 514/380 |
| 5,061,721 | 10/1991 | Cordi et al. | 514/376 |
| 5,086,072 | 2/1992 | Trullas et al. | 514/531 |

FOREIGN PATENT DOCUMENTS

| | | |
|---|---|---|
| 0446699A1 | 9/1991 | European Pat. Off. . |
| 0488959A2 | 6/1992 | European Pat. Off. . |
| 0514023A1 | 11/1992 | European Pat. Off. . |

OTHER PUBLICATIONS

Chemistry News: *Frog Venom Cocktail Yields A One-Handed Painkiller.* (1993) Science 261:1117.

Foster, A. and Fagg, G. (1987) *Taking apart NMDA receptors.* Nature 329:395–396.

Johnson, K. and Jones S. (1990) *Neuropharmacology of Phencyclidine: Basic Mechanisms and Therapeutic Potential.* Annu. Pharmacol. Toxicol. 30:707–750.

Kolesnikov, Y., Pick, C., and Pasternak, G. (1992) $N^G$–Nitro–L–arginine prevents morphine tolerance, Euro. J. of Pharm. 221:399–400.

Kolesnikov, Y., Pick, C., Ciszewska, G., and Pasternak, G. (1993) *Blockade of Tolerance to Morphine But Not Kappa Opioids by a Nitric Oxide Synthase Inhibitor.* Proc. Natl. Acad. Sci. 90:5162–5166.

Luke, M., Hahn, E., Price, M. and Pasternak, G. (1988) *Irreversible opiate agonists and antagonists. V. Novel hydrazone derivatives of naltrexone.* Life Sci. 43:1249–1256.

Mayer, M. and Miller, R. (1990) *Excitatory amino acid receptors, second messengers and regulation of intracellular $Ca^{2+}$ in mammalian neurons.* Trends in Pharmacol. Sci. 11:254–260.

Paul, D., Levinson, J., Howard, D., Pick, C., Hahn, E. and Pasternak, G. (1990) *Naloxone Benzoylhydrazone (NalBzoH) analgesia.* J. Pharmacol. Exp. Ther. 255:769–774.

Paul, D., Pick, C., Tive, L., and Pasternak (1991) *Pharmacological characterization of nalorphine, a $K_3$ analgesic.* J. Pharmoacol. Exp. Ther. 257:1–7.

Ransom, R. and Stec, N. (1988) *Cooperative modulation of [$^{H3}$]MK–801 binding to the N–methyl–D–aspartate receptor–ion channel complex by L–glutamate, glycine, and polyamines.* J. Neurochem. 51:830–836.

Reynolds, I. J. and Miller, R. J. (1989) *Ifenprodil is a novel type of N–methyl–D–aspartate receptor antagonist: interaction with polyamines.* Molec. Pharmacol. 36:758–765.

Trujillo, K. and Akil, H. (1991) *Inhibition of Morphine Tolerance and Dependence by the NMDA Receptor Antagonist MK-801.* Science 251:85–87.

Williams, K., Romano, C., Dichter, M., and Molinoff, P. (1991) *Modulation of the NMDA Receptor by Polyamines.* Life Sci. 48:469–498.

Primary Examiner—Richard L. Raymond
Attorney, Agent, or Firm—Arnall Golden & Gregory

[57] ABSTRACT

This invention concerns inhibitors of the tolerance and dependence induced by opiate analgesics. Excitatory amino acids control the action of the NMDA receptor through allosteric binding sites. Early studies showed that channel blockers and allosteric site antagonists of the NMDA receptor inhibited the development of tolerance to and dependence on opiate analgesics, but also produced their own undesirable side effects. Partial agonists of the NMDA allosteric sites tend to normalize NMDA receptor function and do not produce strong undesirable side effects. It has been discovered that partial agonists inhibit the development of tolerance to opiate analgesics, and it is taught that partial agonists also inhibit development of dependence on opiate analgesics. ACPC, 1-aminocyclopropanecarboxylic acid, in particular, is an exemplary partial agonist at the glycine site useful to treat opiate addiction. Compounds containing an opiate analgesic and a partial agonist, produce analgesia without inducing tolerance or dependence.

38 Claims, 3 Drawing Sheets

USE OF PARTIAL AGONISTS OF THE NMDA RECEPTOR TO REDUCE OPIATE INDUCED TOLERANCE AND DEPENDENCE

FIELD OF THE INVENTION

This invention relates to the NMDA subtype of the glutamate receptor and more specifically to partial agonists of the NMDA allosteric recognition sites which may be used to modulate the response of the NMDA receptor to reduce tolerance and dependence induced by opiate compounds.

BACKGROUND OF THE INVENTION

The search for ways to relieve severe and chronic pain in the human animal has a long and varied history. Even today, the range of available drugs with which to reduce chronic and severe pain is very limited and such drugs often have severe side effects which reduce their effectiveness. The search for new painkillers continues to be a prime area of research and has even recently led to the investigation of the toad venom used by the Ecuadorian Indians in their poison weapons (Chemistry News, Science, 1993). Of the painkilling drugs available, the opiates remain the most useful and widely used. However, continued use of opiates invariably leads to addiction which limits their clinical usefulness.

Addiction has two components, tolerance and dependence. Tolerance is the decreased analgesic effectiveness of a drug with continued use. Its consequence is the necessity to increase the administered dose of the drug to maintain the necessary analgesic effect. In the case of the opiates, particularly morphine, the side effects of prolonged use at the very high doses that sometimes need to be given to sustain analgesia can produce life threatening results. Tolerance is an effect thus seen during the course of analgesic administration. Several drugs have been identified which potentiate (enhance) the effect of a given quantity of opiate, but these drugs can also produce serious side effects. By contrast, dependence is an effect seen only after termination of the repeated administration of a drug. Upon termination, a drug dependant subject experiences mild to severely harsh and unpleasant withdrawal symptoms. Despite the desperately recognized need for drugs which reduce tolerance and dependence and produce no unwanted side effects, the search for such drugs has, up to the time of this invention, been unsuccessful.

Despite intensive research, little has been learned about the underlying mechanisms of addiction. In fact, several opiate receptor mechanisms have been implicated which respond to different opiates each of which may have a separate mechanism responsible for addiction. The development during analgesic treatment of the duality of tolerance and dependence has been likened to a type of learning since it is experience dependant. The analogy of addiction to a learning process has led to the investigation of the relationship of recently discovered biochemical learning associated mechanisms to addiction. In particular, attention has centered on the recent recognition of the role of the excitatory amino acids (EAA) and their associated receptors in both neural plasticity and behavior. EAAs have been discovered to activate their receptors through action at allosteric sites located on the receptors.

NMDA Receptors

Excitatory amino acid (EAA) receptors are broken down into two major subtypes: ionotropic and metabotropic. The ionotropic receptors contain ligand-gated ion channels and mediate ion fluxes for signalling, while the metabotropic receptors use G proteins for signalling. Classification of the ionotropic EAA receptors is based upon the agonists (stimulators) that selectively activate them. Presently, it is believed that there are three major subtypes: a receptor responsive to N-methyl-D-aspartate (NMDA receptors) and two receptors not responsive to NMDA but responsive to $\alpha$-amino- 3-hydroxy-5-methyl-4-isoxazoleproprionic acid (AMPA) and to kainate.

The NMDA receptor controls the flow of both divalent ($Ca^{++}$) and monovalent ($Na^+$, $K^+$) ions into the postsynaptic neural cell, although it is the $CA^{++}$ flux which is of the greatest interest (reviewed in Foster and Fagg, 1987; Mayer and Miller, 1990). Recent work suggests that $Ca^{++}$ is essential for the activation of nitric oxide synthase. Nitric oxide, in turn, modulates cGMP accumulation. The NMDA receptor has been implicated during development in specifying neuronal architecture and synaptic connectivity, and may be involved in experience dependent synaptic modifications. In addition, NMDA receptors are thought to be involved in long term potentiation, CNS plasticity, cognitive processes, memory acquisition, and learning. Furthermore, the NMDA receptor has drawn particular interest since it appears to be involved in a broad spectrum of CNS disorders. For instance, during brain ischemia caused by stroke or traumatic injury, excessive amounts of the excitatory amino acid glutamate are released from damaged or oxygen deprived neurons. This excess glutamate binds to the NMDA receptors which opens their ligand-gated ion channels; in turn the calcium influx produces a high level of intracellular calcium which activates a biochemical cascade resulting in protein degradation and cell death. This phenomenon, known as excitotoxicity, is also thought to be responsible for the neurological damage associated with other disorders ranging from hypoglycemia and cardiac arrest to epilepsy. In addition, there are preliminary reports indicating similar involvement in the chronic neurodegeneration of Huntington's, Parkinson's, and Alzheimer's diseases. Activation of the NMDA receptor has been shown to be responsible for post-stroke convulsions, and, in certain models of epilepsy, activation of the NMDA receptor has been shown to be necessary for the generation of seizures.

Neuropsychiatric involvement of the NMDA receptor has also been recognized since blockage of the NMDA receptor $Ca^{++}$ channel by the animal anesthetic PCP (phencyclidine) produces a psychotic state in humans similar to schizophrenia (reviewed in Johnson, K. and Jones, S., 1990). Further, NMDA receptors have also been implicated in certain types of spatial learning.

The NMDA receptor is believed to consist of several protein chains embedded in the postsynaptic membrane. The two first types of subunits discovered so far form a large extracellular region, which probably contains most of the allosteric binding sites, several transmembrane regions looped and folded so as to form a pore or channel, which is permeable to $Ca^{++}$, and a carboxyl terminal region with an as yet unknown function. The opening and closing of the channel is regulated by the binding of various ligands to domains (allosteric sites) of the protein residing on the extracellular surface. The binding of the ligands is thought to affect a conformational change in the overall structure of the protein which is ultimately reflected in the channel opening, partially opening, partially closing, or closing.

FIG. 1 is a representation of the NMDA receptor showing schematically the principal allosteric recognition/binding sites. The site marked Glu is the receptor site for the principal excitatory amino acid neurotransmitter, glutamate.

This site also binds NMDA. Binding of glutamate/NMDA has been shown to stimulate the flow of $CA^{++}$ through the channel. Thus, glutamate is said to have an agonist (stimulatory) activity. Several competitive inhibitors of the actions of glutamate also bind at this site and include those identified in the box in FIG. 1 labeled NMDA Antagonists. Since these competitive inhibitors of the glutamate site block the flow of $CA^{++}$ through the channel, they are said to have an antagonist activity.

Binding to the glutamate site of the NMDA receptor alone is necessary, but not sufficient, to open the cation channel. It has been found that glycine must also be bound to the receptor for the channel to open. Thus, glycine is also an NMDA receptor agonist. Since glycine binding is not inhibited by glutamate or by competitive inhibitors of glutamate, it is believed that glycine does not bind at the same site as glutamate. Thus, a second and separate binding site for glycine has been proposed as is indicated in FIG. 1 by Gly. The ligand-gated ion channel of the NMDA receptor is, thus, under the control of at least two distinct allosteric sites. Competitive inhibitors of the glycine site are also known and are identified in the box in FIG. 1 labeled Glycine Antagonists. The inhibitors are also NMDA receptor antagonists.

Several compounds are known which are antagonistic to the flow of cations through the NMDA receptor but which do not competitively inhibit the binding of ligands to any of the known allosteric sites. Instead, these compounds bind inside the open cation channel and are generally known as channel blockers. These are shown in FIG. 1 in the box labeled Channel Blockers. In fact, binding of the channel blocker [$^3$H]MK-801 is a good measure of the activation of the NMDA receptor complex. When the channel is open, [$^3$H] MK-801 may freely pass into the channel and bind to its recognition site in the channel. Conversely, when the channel is closed, [$^3$H]MK-801 may not freely pass into the channel and bind. When the channel is partially open (partially closed)less [$^3$H]MK-801 is able to bind than when the channel is fully open.

It should be understood that it is believed that the channel is in constant motion, alternating between a cation passing (open) and a cation blocking (closed) state. It is not known at present whether the agonists or antagonists actually increase or decrease the time during which the channel is open to the flow of ions, or whether they increase or decrease the frequency of opening. Both effects might be occurring at the same time. Thus, the terms "open" and "close" or "agonistic" or "antagonistic" refer to a time averaged affect.

$Mg^{++}$ and $Zn^{++}$ also modulate the NMDA receptor. The exact location of the divalent cation binding sites is still unclear. $Zn^{++}$ appears to be antagonist to channel opening and appears to bind to an extracellular domain. $Mg^{++}$ shows a biphasic activation curve at low concentrations, is an agonist for NMDA receptor function except at high concentrations at which it is an antagonist, and appears to be absolutely necessary for proper receptor functioning. It appears to bind at two sites. There appears to be a voltage dependant binding site for $Mg^{++}$ within the channel and another binding site on the extracellular domain. These sites are indicated in FIG. 1 by $Mg^{++}$ and $Zn^{++}$.

Recently, (Ransom and Stec, 1988; Reynolds and Miller, 1989; reviewed in Williams et al., 1992) a third class of agonists which effect the excitatory synaptic transmission at the NMDA receptor has been identified. These agonists are polyamines, principally the endogenous polyamines spermine and spermidine, which bind to another extracellular allosteric site on the NMDA receptor. In FIG. 1 the polyamine binding site is labeled PA. The polyamines do not bind to the glutamate/NMDA site, the glycine site, or the channel blocker sites. There may be some relation between the extracellular $Mg^{++}$ binding site and the polyamine site but this relationship has not yet been fully elucidated. There is strong evidence accumulating that, like glycine, polyamine binding is necessary, but not sufficient, for properly regulated functioning of the NMDA receptor coupled cation channel. In fact, the polyamine site may be the most complex site yet identified. There appears to be a broad range of polyamine (diamine, triamine, and tetraamine) compounds which will modulate the site, some of which appear to be agonists, others partial agonists, and, finally, some antagonists.

During the past few years several compounds have been identified which exert a dual (agonist/antagonist) effect on the NMDA receptor through the allosteric sites. These compounds are termed "partial agonists". In the presence of the principal site ligand a partial agonist will displace some of the ligand and thus decrease $Ca^{++}$ flow through the receptor. In the absence of or lowered level of the principal site ligand, the partial agonist acts to increase $Ca^{++}$ flow through the receptor channel. In U.S. Pat. No. 5,086,072 Trullas et al. teach the use of partial agonists of the glycine site, 1-aminocyclopropanecarboxylic acid (ACPC) and its derivatives, to reduce excessive activation of the NMDA receptor to treat mood disorders. In U.S. patent application Ser. No. 07/390,745 copending with U.S. Pat. No. 5,086, 072, Skolnick et al. disclose a method of treating neuropsychopharmacological disorders resulting from excessive activation of the NMDA receptor using the same partial agonists of the glycine site. In U.S. Pat. No. 4,904,681 Cordi et al. teach the use of D-cycloserine and its prodrugs as cognitive enhancers. While D-cycloserine has been used as a treatment against Mycobacterium tuberculosis, its CNS toxicity producing neurologic and psychic disturbances has limited its use. In U.S. Pat. No. 5,061,721 Cordi et al. teach that D-cycloserine is a partial agonist of the glycine site on the NMDA receptor and describe its effect in combination with D-alanine on enhancing memory and learning. Cordi et al. suggest, but do not specifically describe, that in some way it is the partial agonist character of D-cycloserine which is responsible for the cognitive enhancement. Thus, Trullas and Skolnick concentrated on the antagonistic properties of partial agonists of the glycine site while Cordi et al. considered the possibility that both agonist and antagonist properties may play a role in the cognitive effects they observed.

In U.S. patent application Ser. No. 07/952,818, filed Sep. 28, 1992, now abandoned, which is incorporated herein by reference, Maccecchini has shown the snail toxin Conantokin-G to be a non-competitive inhibitor of polyamine modulated responses of the NMDA receptor working at a previously unknown NMDA allosteric site, perhaps adjacent to the polyamine site. This site is shown schematically in FIG. 1 and labeled Con-G. In addition, an entirely new class of peptide compounds possessing some of the primary structure and conformational characteristics of Conantokin-G has been identified which are partial agonists of the NMDA receptor acting at a polyamine associated site. These newly discovered partial agonists of the NMDA receptor have differing degrees of agonistic and antagonistic properties and, thus, provide a whole range of modulation of the NMDA receptor. The wide range of modulation possible with these new partial agonist compounds suggests their use to treat a whole range of conditions where the normal functioning of the NMDA receptor has been disrupted or where modulation of the receptor will produce an enhancement of some activity.

Opiate Addiction & NMDA Receptors

In 1991 it was shown (Trujillo and Akil, 1991) that administration of the channel blocker MK-801 inhibited both tolerance and dependence to the opiate morphine in test animals. Further, the observed MK-801 inhibition did not block or potentiate the morphine analgesic action. This suggested that the NMDA receptor was involved in the behavioral changes and probably the neural adaptations seen in addiction at least with respect to the morphine receptors. Subsequently in 1992, (Kolesnikov, Pick, and Pasternak, 1992) it was demonstrated that inhibition of nitric oxide synthase activity, which is normally induced by activation of the NMDA receptor, also inhibited tolerance. Again, this report suggested that NMDA receptor activity was linked to opiate tolerance and dependence.

Recently, this study has been extended (Kolesnikov, Pick, Ciszewska, and Pasternak, 1993) to show that the nitric oxide synthase inhibitor, $N^G$-Nitro-L-arginine, only inhibits tolerance to the mu opiate, morphine, and does not prevent tolerance to analgesia induced by the kappa$_1$ or kappa$_3$ opioids. This suggests that the development of tolerance to different analgesics involves different mechanisms of action and that not all tolerance is mediated through the NMDA receptor. In European patent application No. 92303527.3, Publication No. 0 514 023 A1, a competitive antagonist of the glycine site of the NMDA receptor ([+]-HA-966) is shown by Hudson to prevent or reduce dependence induced by morphine. MK-801, HA-966 and $N^G$-Nitro-L-arginine can produce unacceptable side effects. $N^G$-Nitro-L-arginine irreversibly inhibits nitric oxide synthase, a key component in the biochemistry of the postsynaptic cell. With MK-801 and HA-966, the normal functioning of the NMDA receptor is significantly altered. Indeed, channel blockers such as PCP and MK-801 produce psychotic states in man. Other compounds which competitively inhibit the functioning of the NMDA receptor, such as NMDA antagonists, also interfere with normal brain function and are known to produce psychotomimetic effects. While the competitive inhibitor HA-966's preferential binding to the glycine site inhibits tolerance to morphine, the antagonized state of the NMDA receptor presumably does not allow for normal neural functioning.

With respect to the use of compounds which act at the NMDA receptor to inhibit aspects of opiate addiction, much like the work (except for Maccecchini) with respect to the partial agonists, the prior art teaches that only the cutting off or reduction of ion flow through the NMDA receptor produces an inhibition of aspects of opiate addiction.

SUMMARY OF THE INVENTION

A fundamental concept underlying this invention is the recognition that previous concepts of partial agonists as compounds which merely possessed dual behaviors under certain conditions, one or the other of which could be utilized, concentrated on the details of the dual behavior and missed "the forest for the trees". In fact, partial agonists should be viewed as regulators of NMDA receptor function which always tend to normalize the receptor function through the particular allosteric site where they work. Thus, if the receptor is overstimulated, the partial agonist reduces the flow of $Ca^{++}$; if the receptor is understimulated, the partial agonist increases the flow of $Ca^{++}$. It has been discovered that partial agonists of the NMDA receptor reduce or inhibit the development of tolerance to opiates. It is an object of this invention to use partial agonists of the NMDA receptor's allosteric sites to inhibit the development of tolerance to opiate analgesia by administering to a patient in need thereof an effective amount of a partial agonist. Another object of the present inventions is to use partial agonists of the NMDA receptor's allosteric sites to inhibit the development of dependence on opiate analgesics by administering to a patient in need thereof an effective amount of a partial agonist. A further object of this invention is to provide pharmaceutical compositions of opiates and partial agonists which may be used to minimize or prevent the development of tolerance and dependence to opiate analgesics.

DETAILED DESCRIPTION OF THE INVENTION

Figure 1:
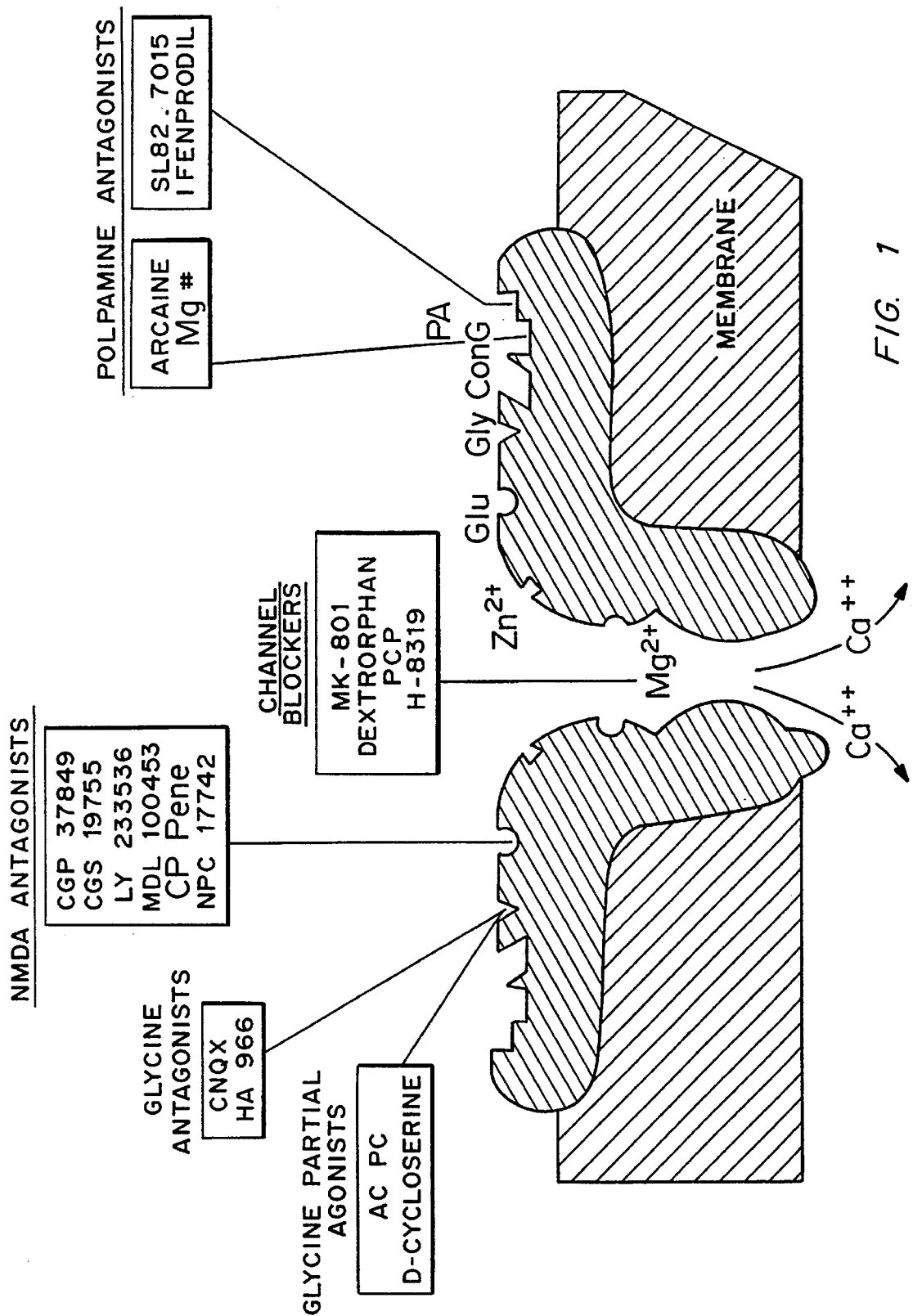
FIG. 1 shows a schematic representation of the known binding sites on the NMDA receptor.

This detailed description is presented in three parts. First, several terms frequently used in this description are defined, some of them because their meanings are not yet standardized in the literature. Second, a brief description of the materials and methods which were used to measure the effects of partial agonists on opiate induced tolerance. Third, so that those skilled in the art may more fully understand and use the invention, scientific examples of the use of the partial agonists are given.

Glossary of Terms

The following terms are defined so that their use in this application is unambiguous:

The term "agonist" as used herein means any compound which increases the flow of $Ca^{++}$ through the NMDA receptor—a channel opener.

The term "ACPC" as used herein means 1-aminocyclopropanecarboxylic acid.

The term "antagonist" as used herein means any compound which reduces the flow of $Ca^{++}$ through the NMDA receptor—a channel closer.

The term "ligand" as used herein means any compound which binds to a site on the NMDA receptor.

The term "opiate" as used herein means:

1) any compound which is derived from opium including, but not limited to thebaine, morphine, diacetylmorphine, hydromorphone, oxycodone, codeine, and oxymorphone;

2) any synthetic opioid acting at the same mu receptor sites as the compounds of subsection (1) hereof including, but not limited to meperidine, pentazocine, methadone, fentanyl, and butorphanol; and 3) any endogenous or synthetic opioid peptides acting at the mu or delta receptors.

The term "NMDA receptor" as used herein means a postsynaptic receptor which is stimulated, at a minimum, by the excitatory amino acids glutamate and glycine. It is a ligand-gated receptor with a strychnine insensitive glycine site.

The term "partial agonist" as used herein means a compound which modulates an allosteric site on the NMDA receptor so as to increase or decrease the flux of $Ca^{++}$ through the ligand-gated channel depending on the presence or absence of the principal site ligand. In the absence of the principal site ligand, a partial agonist increases the flow of $Ca^{++}$ through the ligand-gated channel but at a lower flux than achieved by the principal site ligand—a partial agonist may thus partially open the NMDA receptor channel. In the presence of the principal site ligand, a partial agonist decreases the flow of $Ca^{++}$ through the ligand-gated channel below the flux normally achieved by the principal site ligand—a partial agonist may thus partially close the NMDA receptor channel.

The term "lower alkyl" as used herein means an alkyl radical having 1–9 carbon atoms, which may be straight or branched, including, for example, methyl, ethyl, propyl, isopropyl, butyl, isobutyl, tertbutyl, amyl, isoamyl, hexyl, heptyl, octyl, nonyl, or the like.

The term "halogen" as used herein refers to fluorine, chlorine, bromine, and iodine atoms.

The term "hydroxyl" as used herein means —OH.

The term "lower alkoxy" as used herein means lower alkyl-O—.

The term "oxo" as used herein means an =O group.

The term "mercapto" as used herein means a —SH group.

The term "aryl" as used herein means an organic radical derived from an aromatic hydrocarbon, e.g., phenyl from benzene.

The term "amino" as used herein means —$NH_2$.

The term "pharmaceutically acceptable salt" as used herein includes acid addition salts, ammonium salts, hydrates, alcolates and other salts of Formulas I and II compounds disclosed herein which are physiologically compatible in warm blooded animals, The addition salts may be formed by either strong or weak acids. Representative of strong acids are hydrochloric, sulfuric and phosphoric. Representative of weak acids are fumaric, maleic, succinic, oxalic, citric, tartaric, cyclohexaminic and the like.

Methods and Materials:

Experimental Animals: Male CD-1 mice (25–35 g.; Charles River Breeding Laboratories, Wilmington, Mass.) were maintained on a 12 hr. light: 12 hr. dark cycle with Purina rodent chow and water available ad libitum. Mice were housed in groups of 5 until testing.

Experimental Drugs: Morphine sulfate was obtained from Mallinckrodt (St. Louis, Mo.) and U50,488H {trans-3,4-dichloro-N-methyl-N-[2-(1-pyrrolindinyl)cyclohexyl]-benzeneacetamide, methane sulfonate hydrate} was supplied by Upjohn Pharmaceutics (Kalamazoo, Mich.). Naloxone benzoylhydrazone (NalBzoH) was synthesized as described by Luke et al. (Luke, Hahn, Price, and Pasternadk, 1988). ACPC was obtained from Senn Chemicals, Zurich, Switzerland. The delta peptide [D-Pen2,D-Pen5]enkephalin (DPDPE) was obtained from the Research Technology Branch of NIDA. NaIBzoH was dissolved in 30% ETOH, which did not produce analgesia in control mice, and doses are stated as the free base. All other drugs were dissolved in saline or water.

Experimental Methods: Single daily doses of all analgesics except for DPDPE along with a fixed dose of ACPC were administered subcutaneously to the mice for a period of five to ten days. DPDPE was administered intrathecally on a daily basis. A dose (mg/kg body weight) of analgesic was chosen which would produce analgesia in approximately 50% to 60% of the mice. This value was chosen since it avoided the possibility of using too high a dose which would provide excess analgesia and at the same time would provided a sufficient dose so that the effects of tolerance and the inhibition of tolerance could be studied. Analgesia in the mice was determined using the radiant heat tail-flick technique (Paul, Levinson, Howard, Pick, Hahn, and Pasternak, 1990; Paul, Pick, Tive, and Pasternak, 1991 ). In this analgesic assay, the latency to withdraw the tail from a focussed light stimulus was measured electronically using a photocell. Baseline latencies (2.0–3.0 sec.) were determined before experimental treatments for all animals as the mean of two trials. Post-treatment tail-flick latencies were determined 30 minutes after the analgesic administration. The stimulus was removed after a maximal latency of 10 sec. to minimize tissue damage. Analgesia was defined quantally as a doubling or greater of the baseline values for each mouse. All analgesic values presented represent at least 10 mice. To avoid testing animals on more than 6 days in order to minimize tissue damage, all animals were tested on day 1 after which several groups (n=10 each) were used for the extended duration studies. Dose-response curves were determined using three doses of morphine, with each dose including ten mice. The curves were analyzed using a modification of the BLISS-20 computer program. This program maximizes the log-likelihood function to fit a parallel set of Gaussian normal sigmoid curves to the dose response data (Umans, and Inturrisi, 1981). Single-dose comparisons were analyzed using the Fisher exact test.

Use of Partial Agonists To Inhibit Tolerance and Dependence

As indicated above, the prior art teaches that antagonists of the NMDA receptor, i.e., compounds which reduce the $Ca^{++}$ ion flow, are required to inhibit the development of tolerance and dependence. In addition, inhibiting nitric oxide synthase, which is biochemically equivalent to reducing $Ca^{++}$ ion flux through the NMDA receptor with an antagonist, also inhibits dependence. The discovery of this invention that partial agonists have a similar effect is unexpected and surprising. Applicant believes that the prior art has too narrowly concentrated on the individual separate agonistic and antagonistic effects of the partial agonists and that partial agonists should be viewed as regulators of NMDA receptor function which always tend to normalize the receptor function. The fact that the use of partial agonists does not produce the neurotoxic side effects seen with competitive or non-competitive (channel blocker) antagonists of the NMDA receptor supports the view that the partial agonists normalize NMDA function. By utilizing the partial agonists, as described herein, it is possible to treat tolerance and dependence induced by opiate analgesics without producing unwanted side effects such as schizophrenia-like symptoms, loss of normal NMDA receptor-mediated synaptic plasticity (which can possibly affect learning and memory), amnesia, confusional states, and muscle relaxation. This unexpected beneficial result may provide, at long last, a solution to several vexing problems involving the use of opiates including the management of chronic pain in severely ill patients and alleviation of the pain of withdrawal both in legitimate and illegitimate drug users.

Several partial agonists of the NMDA receptor are known which work at either the glycine site or the polyamine associated site such as D-cycloserine and the Con-G derivatives disclosed in the Maccecchini patent application cited earlier, and all are considered within the scope of the present invention. Other suitable compounds useful in this invention include partial agonists of the glycine site having the following Formulas I and II below:

Formula I:

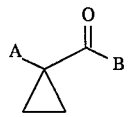

wherein

A is —NH$_2$, —NHR$^1$ or —NR$^1$R$^2$;

B is —OH or —OR$^3$;

R$^1$, R$^2$, and R$^3$, same or different, are selected from lower alkyl and lower alkyl substituted by halogen, hydroxyl, alkoxy, oxo, mercapto, aryl or amino; or a pharmaceutically acceptable salt thereof.

Formula II:

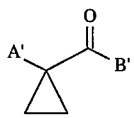

wherein

A$^1$ is —NH$_2$, —NHR$^1$ or —NR$^1$R$^2$,

B$^1$ is —OH or —OR$^3$

R$^1$, R$^2$ and R$^3$, same or different, are lower alkyl, or a pharmaceutically acceptable salt thereof.

The partial agonists of Formulas I & II are exemplified by 1-aminocyclopropanecarboxylic acid (ACPC). While the experimental results presented below were obtained with ACPC, this is in no way to be construed as limiting applicant's general disclosure herein of a method and compounds for inhibiting tolerance and dependence induced by opiate analgesics. Applicant considers within the scope of this disclosure relating to inhibition of opiate induced tolerance and dependence, all partial agonists of the NMDA receptor including, but not limited to, those presently identified for the glycine and polyamine associated sites. Further, it is believed that the herein disclosed use for partial agonists will encourage further discovery efforts to identify natural or synthetic compounds having potentially even broader ranges of partial agonist activity which may be used to alleviate the suffering produced by tolerance and dependence on opiate analgesics.

Figure 2:
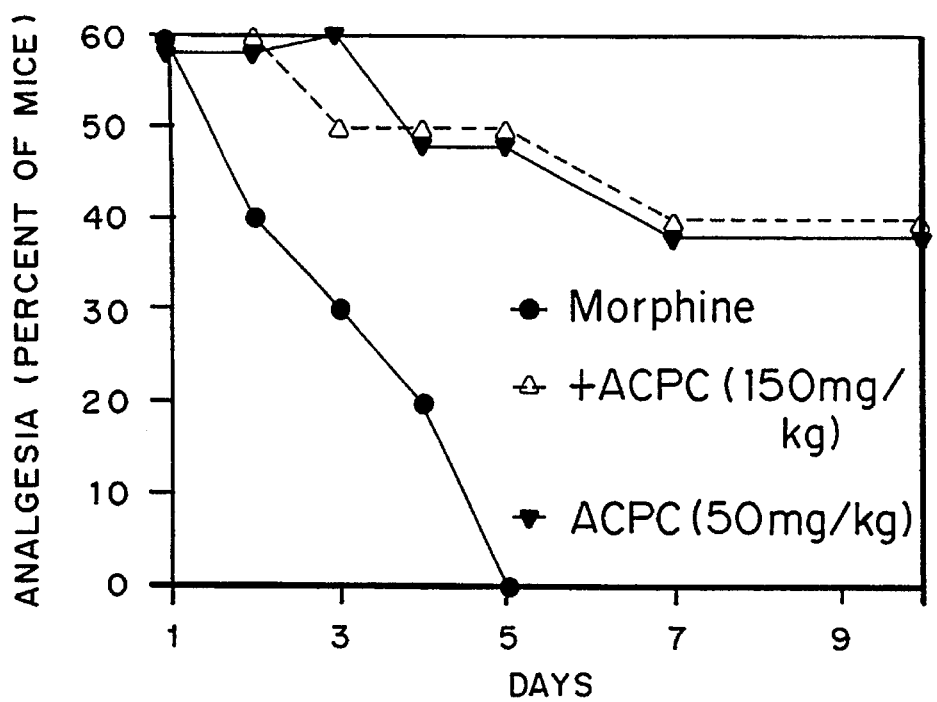
FIG. 2 is a graph of measured analgesia in mice produced by morphine which shows both the development of tolerance to a constant dose of morphine and the inhibition of that tolerance when the same dose of morphine is administered with two different doses of ACPC (150 mg/kg and 50 mg/kg) to different groups of test animals.

The inhibition of the development of tolerance to the opiate morphine and the opioids DPDPE, U50,488H, and NalBzoH by the partial agonist ACPC was studied in mice by administering single daily constant doses of each analgesic along with a fixed dose of ACPC for a period of five to ten days. The extent of analgesia was measured using the tail-flick assay. FIG. 2 shows the effects of ACPC on the development of tolerance to morphine. The solid oval curve of FIG. 2 demonstrates that the animals developed typical analgesic tolerance to the morphine. The dose of morphine which was sufficient to produce analgesia in 60% of the animals on day 1 produced 2 no analgesia by day 5. This curve is typical of the phenomenon of tolerance as also seen in humans. However, the administration of ACPC along with the morphine inhibited the development of tolerance to morphine as can be seen in the open and solid triangle curves of FIG. 2. ACPC significantly retarded the development of tolerance to morphine. At five days, the analgesic response of the ACPC treated animals was not much different than the response of the animals at day 1 but was significantly different from the animals receiving no ACPC who exhibited no analgesic effect of the morphine. Further, even after ten days ACPC inhibited the development of tolerance. Lowering the dose of ACPC to 50 mg/kg yielded virtually identical results demonstrating that ACPC effectively inhibits tolerance at very low dose levels. Animal studies carried out on monkeys have demonstrated that acute administration of ACPC does not produce noticeable side effects until 2.0 g/kg of body weight is given. Further, acute administration to monkeys of up to 8 g/kg ACPC is not lethal. These levels represent extraordinarily high doses; much greater than needed for therapies. In other animal studies, an injection of 300 mg/kg has been found to yield a concentration of 500 µM in brain tissue. Further, in vitro studies on rodent derived NMDA receptors have demonstrated the effect of ACPC at concentrations of 1–5 µM. ACPC may also be administered orally.

The effects seen in FIG. 2 were not due to any analgesic effect produced by ACPC itself and ACPC does not potentiate the effect of morphine. Table 1 below demonstrates the effect of ACPC on morphine analgesia.

TABLE 1

| Effect of ACPC on Morphine Analgesia | |
|---|---|
| ACPC Treatment | Morphine ED$_{50}$ (mg/kg) |
| None | 4.4 (3.6, 5.3) |
| Acute | 4.6 (3.2, 6.5) |
| Chronic | 3.9 (2.4, 5.7) |

Mice were given ACPC (150 mg/kg) either immediately before performing a morphine dose-response curve (acute) or daily for 5 days before determining the morphine ED$_{50}$ (chronic). ED$_{50}$ values were determined using at least three groups of mice, each comprised of 10 subjects. The values in parentheses are the 95% confidence limits for the determination.

Acutely, ACPC (150 mg/kg) did not change morphine's ED$_{50}$. Chronic administration of ACPC followed by analgesic testing of morphine also did not significantly change morphine's analgesic potency. These results are very similar to those seen with NMDA antagonists including MK-801.

Figure 3:
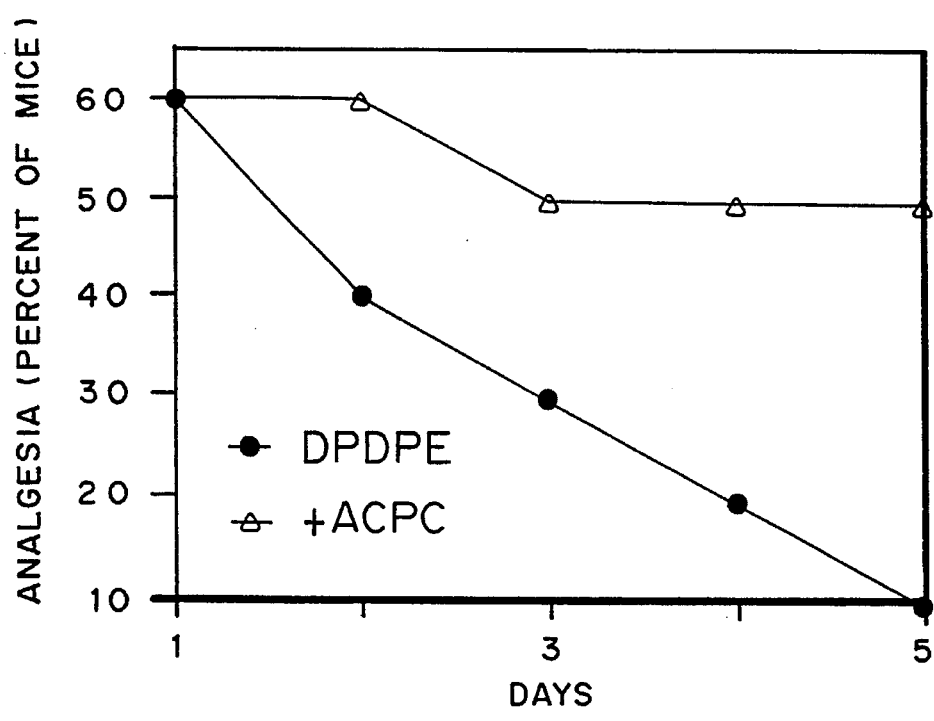
FIG. 3 is a graph of measured analgesia in mice produced by DPDPE which shows both the development of tolerance to a constant dose of DPDPE and the inhibition of that tolerance when the same dose of DPDPE is administered with 150 mg/kg of ACPC to another group of test animals.

FIG. 3 shows the effect of ACPC (150 mg/kg) on the development of tolerance to DPDPE, a synthetic peptide enkephalin analog, which acts at a delta receptor instead of at a mu receptor as does morphine. After five days without ACPC, as shown by the solid oval curve, the test animals developed a tolerance to DPDPE. The difference between the 10% analgesic value indicated on the graph and 0% is not considered statistically significant in this measure. Daily administration of ACPC at 150 mg/kg, as shown by the open triangle curve, inhibited the development of tolerance in a manner similar to the inhibition of morphine tolerance. ACPC virtually eliminated the tolerance seen at five days. Thus, ACPC inhibits the development of tolerance to a delta receptor ligand as well as to a mu receptor ligand.

Figure 4:
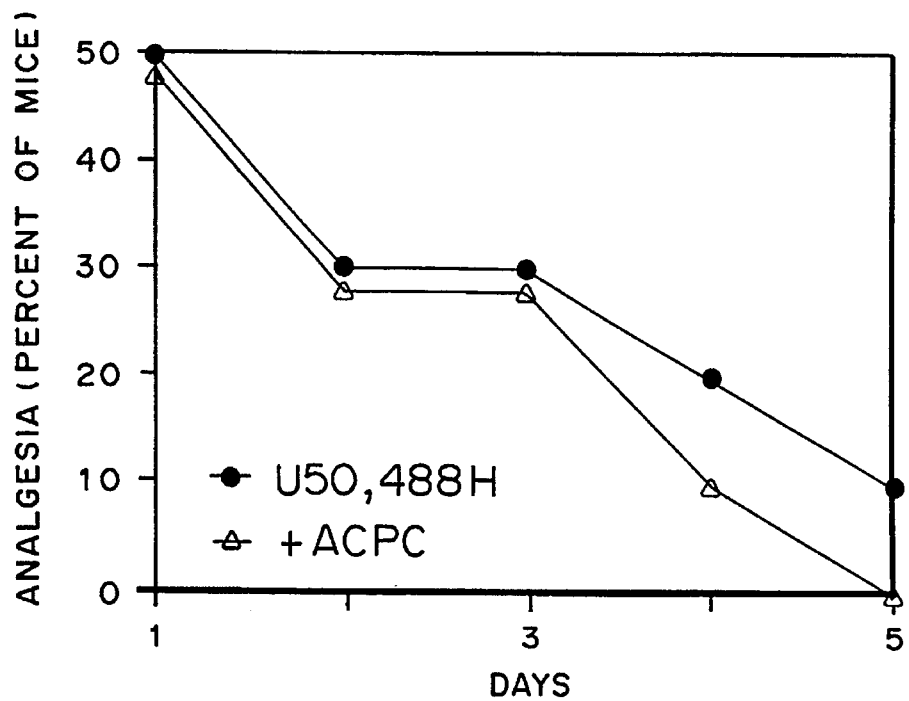
FIG. 4 is a graph of measured analgesia in mice produced by the kappa$_1$ compound U50,488H which shows both the development of tolerance to a constant dose of U50,488H and the lack of inhibition of that tolerance when the same dose of U50,488H is administered with 150 mg/kg of ACPC to another group of test animals.
Figure 5:
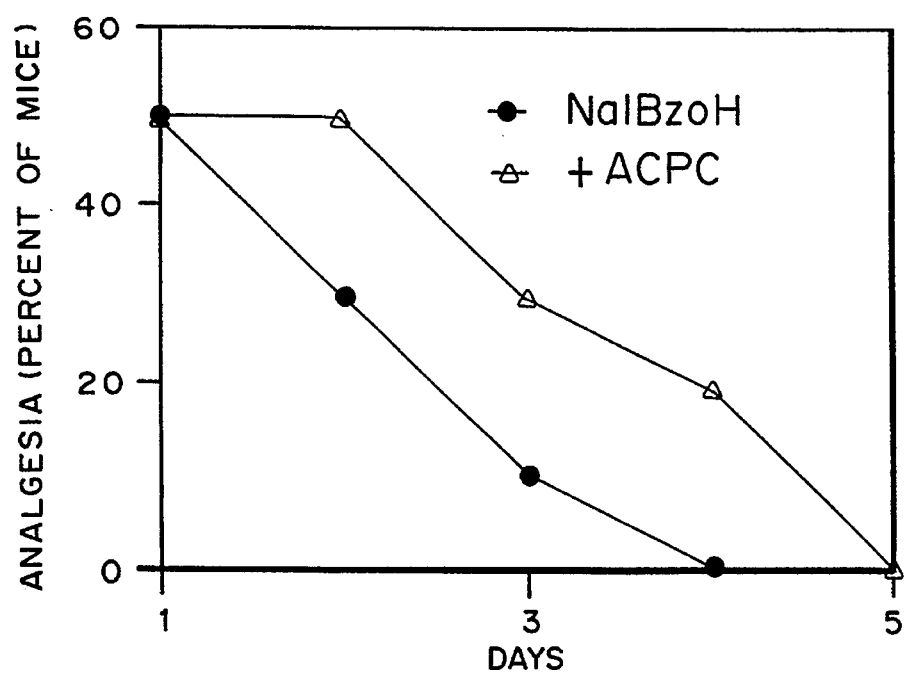
FIG. 5 is a graph of measured analgesia in mice produced by the kappa$_3$ compound NalBzoH which shows both the development of tolerance to a constant dose of NalBzoH and the lack of inhibition of that tolerance when the same dose of NalBzoH is administered with 150 mg/kg of ACPC to another group of test animals.

FIG. 4 shows the effect of ACPC at 150 mg/kg on the development of tolerance to U50,488H, a $kappa_1$ analgesic. Essentially, ACPC does not prevent the development of tolerance to the $kappa_1$ analgesic. FIG. 5 shows the effect of ACPC at 150 mg/kg on the development of tolerance to NalBzoH, a $kappa_3$ analgesic. As with the $kappa_1$ analgesic, ACPC does not prevent the development of tolerance to the kappa3 analgesics. These results parallel those seen with the $kappa_1$ and $kappa_3$ analgesics and the nitric oxide synthase inhibitor $N^G$-Nitro-L-arginine (Kolesnikov, Pick, Ciszewska, and Pasternak, 1993).

From the above it can be seen that a partial agonist of the glycine site on the NMDA receptor inhibits the development of tolerance to morphine in a manner similar to that seen with the channel blocker MK-801 and the nitric oxide synthase inhibitor $N^G$-Nitro-L-arginine. Since MK-801 and HA-966, a competitive antagonist for the glycine site, also inhibit the development of dependence, it is part of the teaching of the present invention that partial agonists of allosteric sites on the NMDA receptor also inhibit the development of dependence. Accordingly, this invention encompasses the use of partial agonists to inhibit the development of dependence. It is also reasonable to expect that compositions comprising several partial agonists, having activities either at the same site or at different sites, may be particularly effective in inhibiting development of tolerance and dependence, and such simultaneous use of multiple partial agonists is also within the scope of this invention.

Pharmaceutical Compositions

The partial agonists of Formula I and II of this invention may be formulated into sterile pharmaceutical compositions for injection by combination with appropriate pharmaceutically acceptable carriers or diluents or may be formulated into preparations in liquid or solid forms for other routes of administration. Administration of the compounds of Formula I & II can be by any technique which delivers the compounds into the bloodstream including oral administration, and by intravenous, intramuscular, or subcutaneous injection. The following methods and excipients are, therefore, merely exemplary and are in no way to be construed as limiting the present inventive methods or compositions.

In pharmaceutical dosage forms, partial agonists of Formulas I & II encompassed by the present invention may be used in the form of their pharmaceutically acceptable salts, and may also be used alone or in appropriate association, as well as in combination with other pharmaceutically active compounds such as dependence-inducing and tolerance-inducing compounds. The compounds of Formulas I & II may be formulated into preparations for injection by dissolving, suspending or emulsifying them in an aqueous or non-aqueous solvent, such as vegetable oil, synthetic aliphatic acid glycerides, esters of higher aliphatic acids or propylene glycol; and, if desired, with conventional additives such as solubilizers, isotonic agents, suspending agents, emulsifying agents, stabilizers and preservatives.

Alternatively, if an oral dosage is desired containing the partial agonists of Formulas I & II this invention alone or the partial agonists in combination with tolerance-inducing and dependence-inducing compounds, commonly used and pharmaceutically acceptable tabletting excipients, such as lactose, microcrystalline cellulose, corn starch stearic acid, or the like, may be used, if desired, to prepare such dosage forms.

The amount of the partial agonist compounds of the present invention to be used may vary according to the degree of tolerance or dependence exhibited and may be adjusted for increases or decreases in the dosage of the tolerance-inducing or dependence-inducing compounds administered as well as the period of time during which such tolerance-inducing or dependence-inducing compounds are administered. Nonetheless, when the compounds of Formula I and II are injected, a suitable dosage is thought to be about 0.1 to 20 mg/kg body weight, and preferably 2 to 10 mg/kg body weight. The most preferred dosages is, of course, that amount sufficient to inhibit tolerance or dependence in the subject.

The partial agonists of this invention may be formulated into unit dosage forms, wherein the term "unit dosage" refers to physically discrete units suitable as unitary dosages for human subjects, each unit containing a predetermined quantity of a partial agonist either alone or in conjunction with a dependence-inducing or toleranceinducing compound, calculated in an amount sufficient with a pharmaceutically acceptable diluent, carrier, or vehicle. The specification for such unit dosage forms depends on the particular partial agonist or partial agonist and tolerance-inducing or dependence-inducing compound employed and the effect to be achieved, and the pharmacodynamics associated with each compound in the treated subject. Any necessary adjustments in dose can be readily made to meet the needs of a given subject by the skilled practitioner.

Although the invention has been described with reference to ACPC as representative of the compounds of Formulas I & II, which in turn are representative of all partial agonists of the NMDA receptor, this should not be construed as a limitation on the invention. Rather, various other partial agonists, equivalents, modifications, and other derivatives as would be obvious to one skilled in the art upon learning of the invention and without departing from the spirit and scope of the invention are intended to be included within the scope of the disclosure and of the following claims.

References Cited

1. Chemistry News: *Frog Venom Cocktail Yields A One-Handed Painkiller.* (1993) Science 261:1117.
2. Foster, A. and Fagg, G. (1987) *Taking apart NMDA receptors.* Nature 329:395–396.
3. Johnson, K. and Jones, S. (1990) *Neuropharmacology of Phencyclidine: Basic Mechanisms and Therapeutic Potential.* Annu. Rev. Pharmacol. Toxicol. 30:707–750.
4. Kolesnikov, Y., Pick, C., and Pasternak, G. (1992) *$N^G$-Nitro-L-arginine prevents morphine tolerance.* Euro. J. of Pharm. 221:399–400
5. Kolesnikov, Y., Pick, C., Ciszewska, G., and Pasternak, G. (1993) Blockade of *Tolerance to Morphine But Not Kappa Opioids by a Nitric Oxide Synthase Inhibitor.* Proc. Natl. Acad. Sci. 90:5162–5166
6. Luke, M., Hahn, E., Price, M., and Pasternak, G. (1988) *Irreversible opiate agonists and antagonists. V. Novel hydrazone derivatives of naltrexone.* Life Sci. 43:1249–1256

7. Mayer, M. and Miller, R. (1990) *Excitatory amino acid receptors, second messengers and regulation of intracellular $Ca^{2+}$ in mammalian neurons.* Trends in Pharmacol. Sci. 11:254–260.
8. Paul, D., Levinson, J., Howard, D., Pick, C., Hahn, E. and Pasternak, G. (1990) *Naloxone Benzoylhydrazone (NalBzoH) analgesia.* J. Pharmacol. Exp. Ther. 255:769–774
9. Paul, D., Pick, C., Tive, L., and Pasternak (1991) *Pharmacological characterization of nalorphine, a $K_3$ analgesic.* J. Pharmacol. Exp. Ther. 257:1–7
10. Ransom, R. and Stec, N. (1988) *Cooperative modulation of [$^3H$]MK-801 binding to the N-methyl-D-aspartate receptor-ion channel complex by L-glutamate, glycine, and polyamines.* J. Neurochem. 51:830–836.
11. Reynolds, I. J. and Miller, R. J. (1989) *Ifenprodil is a novel type of N-methyl-D-aspartate receptor antagonist: interaction with polyamines.* Molec. Pharmacol. 36:758–765.
12. Trujillo, K. and Akil, H. (1991) *Inhibition of Morphine Tolerance and Dependence by the NMDA Receptor Antagonist MK-801.* Science 251:85–87.
13. Umans, J. and Inurrisi, C. (1981) *Pharmacodynamics of subcutaneously administered diacetylmorphine, 6-acetylmorphine and morphine in mice.* J. Pharmacol. Exp. Ther. 218:409–415
14. Williams, K., Romano, C., Dichter, M., and Molinoff, P. (1991) *Modulation of the NMDA Receptor by Polyamines.* Life Sci. 48:469–498

I claim:

1. A method of reducing tolerance to opiate drugs comprising administering to a patient in need thereof a therapeutically effective amount of a compound processing partial agonist properties for an allosteric site on the NMDA receptor.

2. The method of claim 1 wherein the partial agonist is a compound having the formula: I

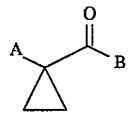

wherein
A is —$NH_2$, —$NHR^1$ or —$NR^1R^2$;
B is —OH or —$OR^3$;
$R^1$, $R^2$, and $R^3$, same or different, are selected from lower alkyl and lower alkyl substituted by halogen, hydroxyl, alkoxy, oxo, mercapto, aryl or amino; or a pharmaceutically acceptable salt thereof.

3. The method of claim 1 wherein the partial agonist is 1-aminocyclopropanecarboxylic acid.

4. The method of claim 1 wherein the partial agonist is a compound having the formula: II

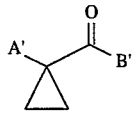

where
$A^1$ is —$NH_2$, —$NHR^1$ or —$NR^1R^2$,
$B^1$ is —OH or —$OR^3$
$R^1$, $R^2$ and $R^3$, same or different, are lower alkyl, or a pharmaceutically acceptable salt thereof.

5. The method of claim 1 wherein the opiate drug is morphine.

6. The method of claim 5 wherein the partial agonist is a compound having the formula: I

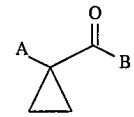

wherein
A is —$NH_2$, —$NHR^1$ or —$NR^1R^2$;
B is —OH or —$OR^3$;
$R^1$, $R^2$, and $R^3$, same or different, are selected from lower alkyl and lower alkyl substituted by halogen, hydroxyl, alkoxy, oxo, mercapto, aryl or amino; or a pharmaceutically acceptable salt thereof.

7. The method of claim 6 wherein the partial agonist is 1-aminocyclopropanecarboxylic acid.

8. The method of claim 5 wherein the partial agonist is a compound having the formula: II

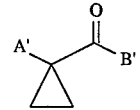

wherein
$A^1$ is —$NH_2$, —$NHR^1$ or —$NR^1R^2$,
$B^1$ is —OH or —$OR^3$
$R^1$, $R^2$ and $R^3$, same or different, are lower alkyl, or a pharmaceutically acceptable salt thereof.

9. A method of reducing tolerance to opiate drugs comprising administering to a patient in need thereof a therapeutically effective amount of a compound processing partial agonist properties for the glycine allosteric site on the NMDA receptor.

10. The method of claim 9 wherein the partial agonist is a compound having the formula: I

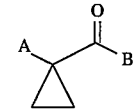

wherein
A is —$NH_2$, —$NHR^1$ or —$NR^1R^2$;
B is —OH or —$OR^3$;
$R^1$, $R^2$, and $R^3$, same or different, are selected from lower alkyl and lower alkyl substituted by halogen, hydroxyl, alkoxy, oxo, mercapto, aryl or amino; or a pharmaceutically acceptable salt thereof.

11. The method of claim 10 wherein the partial agonist is 1-aminocyclopropanecarboxylic acid.

12. The method of claim 9 wherein the partial agonist is a compound having the formula: II

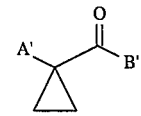

wherein
$A^1$ is —$NH_2$, —$NHR^1$ or —$NR^1R^2$,
$B^1$ is —OH or —$OR^3$
$R^1$, $R^2$ and $R^3$, same or different, are lower alkyl, or a pharmaceutically acceptable salt thereof.

13. The method of claim 9 wherein the opiate drug is morphine.

14. The method of claim 13 wherein the partial agonist is a compound having the formula:

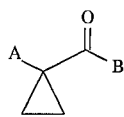

wherein

A is —NH$_2$, —NHR$^1$ or —NR$^1$R$^2$;

B is —OH or —OR$^3$;

R$^1$, R$^2$, and R$^3$, same or different, are selected from lower alkyl and lower alkyl substituted by halogen, hydroxyl, alkoxy, oxo, mercapto, aryl or amino; or a pharmaceutically acceptable salt thereof.

15. The method of claim 14 wherein the partial agonist is 1-aminocycopropanecarboxylic acid.

16. The method of claim 13 wherein the partial agonist is a compound having the formula: II

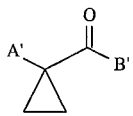

wherein

A$^1$ is —NH$_2$, —NHR$^1$ or —NR$^1$R$^2$,

B$^1$ is —OH or —OR$^3$

R$^1$, R$^2$ and R$^3$, same or different, are lower alkyl, or a pharmaceutically acceptable salt thereof.

17. A method of reducing depenance on opiate drugs comprising administering to a patient in need thereof a therapeutically effective amount of a compound processing partial agonist properties for an allosteric site on the NMDA receptor.

18. The method of claim 17 wherein the partial agonist is a compound having the formula: I

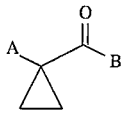

wherein

A is —NH$_2$, —NHR$^1$ or —NR$^1$R$^2$;

B is —OH or —OR$^3$;

R$^1$, R$^2$, and R$^3$, same or different, are selected from lower alkyi and lower alkyl substituted by halogen, hydroxyl, alkoxy, oxo, mercapto, aryl or amino; or a pharmaceutically acceptable salt thereof.

19. The method of claim 18 wherein the partial agonist is 1-aminocyclopropanecarboxylic acid.

20. The method of claim 17 wherein the partial agonist is a compound having the formula: II

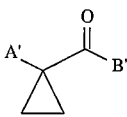

wherein

A$^1$ is —NH$_2$, —NHR$^1$ or —NR$^1$R$^2$,

B$^1$ is —OH or —OR$^3$

R$^1$, R$^2$ and R$^3$, same or different, are lower alkyl, or a pharmaceutically acceptable salt thereof.

21. The method of claim 17 wherein the opiate drug is morphine.

22. The method of claim 21 wherein the partial agonist is a compound having the formula: I

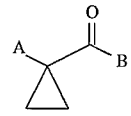

wherein

A is —NH$_2$, —NHR$^1$ or —NR$^1$R$^2$;

B is —OH or OR$^3$;

R$^1$, R$^2$, and R$^3$, same or different, are selected from lower alkyl and lower alkyl substituted by halogen, hydroxyl, alkoxy, oxo, mercapto, aryl or amino; or a pharmaceutically acceptable salt thereof.

23. The method of claim 22 wherein the partial agonist is 1-aminocyclopropanecarboxylic acid.

24. The method of claim 21 wherein the partial agonist is a compound having the formula: II

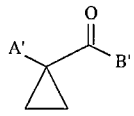

wherein

A$^1$ is —NH$_2$, —NHR$^1$ or —NR$^1$R$^2$,

B$^1$ is —OR or —OH$^3$

R$^1$, R$^2$ and R$^3$, same or different, are lower alkyl, or a pharmaceutically acceptable salt thereof.

25. A method of reducing dependance on opiate drugs comprising administering to a patient in need thereof a therapeutically effective amount of a compound possessing partial agonist properties for the glycine allosteric site on the NMDA receptor.

26. The method of claim 25 wherein the partial agonist is a compound having the: formula: I

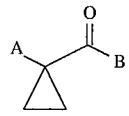

wherein

A is —NH$_2$, —NHR$^1$ or 13 NR$^1$R$^2$;

B is —OH or —OR$^3$;

R$^1$, R$^2$, and R$^3$, same or different, are selected from lower alkyl and lower alkyl substituted by halogen, hydroxyl, alkoxy, oxo, mercapto, aryl or amine; or a pharmaceutically acceptable salt thereof.

27. The method of claim 26 wherein the partial agonist is 1-aminocyclopropanecarboxylic acid.

28. The method of claim 25 wherein the partial agonist is a compound having the formula: II

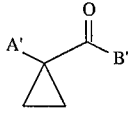

wherein

A¹ is —NH₂, —NHR¹ or —NR¹R²,

B¹ is —OH or —OR³

R¹, R² and R³, same or different, are lower alkyl, or a pharmaceutically acceptable salt thereof.

29. The method of claim 25 wherein the opiate drug is morphine.

30. The method of claim 29 wherein the partial agonist is a compound having the formula: I

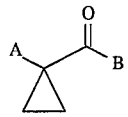

wherein

A is —NH₂, —NHR¹ or —NR¹R²;

B is —OH or —OR³;

R¹, R², and R³, same or different, are selected from lower alkyl and lower alkyl substituted by halogen, hydroxyl, alkoxy, oxo, mercapto, aryl or amino; or a pharmaceutically acceptable salt thereof.

31. The method of claim 30 wherein the partial agonist is 1-aminocyclopropanecarboxylic acid.

32. The method of claim 29 wherein the partial agonist is a compound having the formula: II

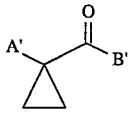

wherein

A¹ is —NH², —NHR¹ or —NR²,

B¹ is —OH or —OR³

R¹, R² and R³, same or different, are lower alkyl, or a pharmaceutically acceptable salt thereof.

33. A pharmaceutical composition comprising an opiate analgesic and a partial agonist of the NMDA receptor.

34. The composition of claim 33 wherein the partial agonist is a compound having the formula: I

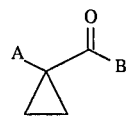

wherein

A is —NH₂, —NHR¹ or —NR¹R²;

B is —OH or —OR³;

R¹, R², and R³, same or different, are selected from lower alkyl and lower alkyl substituted by halogen, hydroxyl, alkoxy, oxo, mercapto, aryl or amino; or a pharmaceutically acceptable salt thereof.

35. The composition of claim 34 wherein the partial agonist is 1-aminocyclopropanecarboxylic acid.

36. The composition of claim 33 wherein the partial agonist is a compound having the formula: II

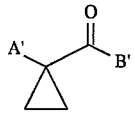

wherein

A¹ is —NH₂, —NHR¹ or —NR¹R²,

B¹ is —OH or —OR³

R¹, R² and R³, same or different, are lower alkyl, or a pharmaceutically acceptable salt thereof.

37. A method of reducing tolerance to a tolerance-inducing agent, the effects of which are mediated through the NMDA receptor, the method comprising administering to a patient in need thereof a therapeutically effective amount of a compound possessing partial agonist properties for an allosteric site on the NMDA receptor.

38. A method of reducing dependence on a dependence-inducing agent, the effects of which are mediated through the NMDA receptor, the method comprising administering to a patient in need thereof a therapeutically effective amount of a compound possessing partial agonist properties for an allosteric site on the NMDA receptor.

* * * * *

UNITED STATES PATENT AND TRADEMARK OFFICE
CERTIFICATE OF CORRECTION

PATENT NO : 5,523,323
DATED : June 4, 1996
INVENTOR(S) : Maria-Luisa Maccecchini It is certified that error appears in the above-identified patent and that said Letters Patent is hereby corrected as shown below:

Claim 1, column 13, line 32, cancel "processing" and insert --possessing--.

Claim 9, column 14, line 34, cancel "processing" and insert --possessing--.

Claim 17, column 15, line 34, cancel "depenance" and insert --dependence--.

Claim 17, column 15, line 36, cancel "processing" and insert --possessing--.

Claim 25, column 16, line 37, cancel "dependance" and insert --dependence--.

Signed and Sealed this

Sixth Day of February, 2001

*Attest:*

Q. TODD DICKINSON

*Attesting Officer*    Director of Patents and Trademarks